United States Patent [19]

Briggs et al.

[11] Patent Number: 5,563,054

[45] Date of Patent: Oct. 8, 1996

[54] PROCESS FOR PREPARATION OF BENZO[B]THIOPHENE GLUCURONIDES

[75] Inventors: Barbara S. Briggs, Indianapolis; Milton J. Zmijewski, Jr., Carmel, both of Ind.

[73] Assignee: Eli Lilly and Company, Indianapolis, Ind.

[21] Appl. No.: 414,962

[22] Filed: Mar. 31, 1995

[51] Int. Cl.$^6$ .............................. C12N 1/12; C12N 1/20; C12P 15/00

[52] U.S. Cl. .................. 435/127; 435/252.1; 435/253.5; 435/253.6

[58] Field of Search ............................ 435/127, 252.1, 435/253.5, 253.6

[56] References Cited

U.S. PATENT DOCUMENTS

| | | | |
|---|---|---|---|
| 4,418,068 | 11/1983 | Jones | 424/267 |
| 5,057,522 | 10/1991 | Chen et al. | 514/303 |
| 5,085,992 | 2/1992 | Chen et al. | 435/119 |
| 5,217,882 | 6/1993 | Chen | 435/85 |

FOREIGN PATENT DOCUMENTS 584952  3/1994  European Pat. Off. .

OTHER PUBLICATIONS

T. S. Chen et al., "Microbial Hydroxylation and Glucuronidation of the Angiotensin II (AII) Receptor Antagonist MK 954", *J. Antibiot.*, 46(1), 131–134 (1993).

C. A. Frolik et al., "In Vivo and In Vitro Metabolism of Raloxifene", *Am. Soc. Bone and Mineral Res.*, Tampa, FL, Sep. 18–22, 1993.

T. B. Lindstrom et al., "Disposition and Metabolism of New Benzthiophene Anteistrogen in Rats, Dogs, Monkeys", *Xenobiotica*, 14(11), 841–847 (1984).

L. J. Black et al., "The Relationship of the Antiestrogenic Efficacy of LY156758 to its Pharmacokinetics and Metabolism Following Oral Administration to Adult Ovariectomized Rats", 7th Int'l Congress of Endocrin., Quebec City, Canada, Jul. 1–7, 1984.

*Primary Examiner*—John W. Rollins
*Assistant Examiner*—Deborah K. Ware
*Attorney, Agent, or Firm*—James P. Leeds; David E. Boone

[57] ABSTRACT

The present invention provides a biotransformation process for preparing a compound of the formula

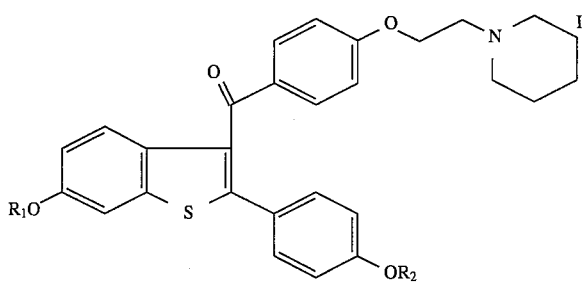

wherein $R_1$ and $R_2$ are hydrogen or a β-glucuronide group of the formula

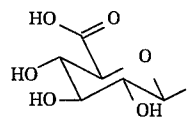

provided at least one of $R_1$ and $R_2$ is a β-glucuronide group.

9 Claims, No Drawings

PROCESS FOR PREPARATION OF BENZO[B]THIOPHENE GLUCURONIDES

BACKGROUND OF THE INVENTION

A 3-aroyl-2-arylbenzo[b]thiophene recently has been clinically evaluated for use in treating and/or preventing osteoporosis. Specifically, 6-hydroxy-2-(4-hydroxyphenyl)-3 -[4-(2-piperidinoethoxy)benzoyl]benzo[b]thiophene, also known as raloxifene, has been clinically tested for such use. In addition to the ability to inhibit bone resorption and bone loss, this compound also is effective in lowering serum cholesterol levels. Interestingly, following oral administration, this compound is extensively conjugated to a glucuronidated form. See Lindstrom et al., *Xenobiotica*, 14(11), 841–847 (1984). This glucuronide conjugate displays significant antiestrogenic and antiuteronropic activity. In various tissues, the conjugated or glucuronidated form is converted to raloxifene in vivo. See Frolik, *Am. Soc. Bone and Mineral Research*(ASBMR), Tampa, Fla., Sep. 12–18 (1993).

A synthesis of the various glucuronidated forms was required to assign a chemical structure to the metabolically conjugated form of raloxifene. Small quantities of two different monoglucuronides of raloxifene, the 4'-glucuronide and the 6-glucuronide, were produced by biotransformation using NIH3T3 cells. See Frolik, *Am. Soc. Bone and Mineral Research* (ASBMR), Tampa, Fla., Sep. 12–18 (1993). This process was suitable for the preparation of chromatographic standards of the glucuronides; however, this process is not suitable for large-scale synthesis of these glucuronides. Large quantities of these glucuronides are needed to study the pharmacokinetics and toxicity of these compounds. Because the multi-step chemical routes for synthesizing these glucuronides produce these compounds in Low yields, an efficient biotransformation process is desired.

Glucuronides of anti-hypertensive compounds are prepared by biotransformation using a culture of Streptomyces sp. MA6751. These compounds are N2-tetrazoyl β-glucuronides, wherein the glucuronidation occurs on the tetrazole group of the anti-hypertensive compound. See U.S. Pat. Nos. 5,057,522 and 5,085,922, and Chin et al., *J. Antibiot.*, 46(1), 131–134 (1993).

SUMMARY OF THE INVENTION

The present invention relates to a biotransformation process for the preparation of benzo[b]thiophene glucuronides. More specifically, the present invention relates to a process for preparing a compound of the formula

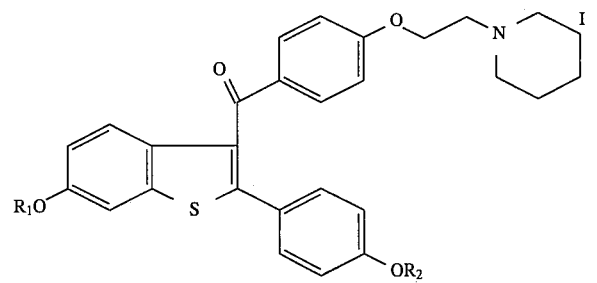

wherein $R_1$ and $R_2$ are hydrogen or a β-glucuronide group of the formula

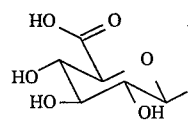

provided at least one of $R_1$ and $R_2$ is a β-glucuronide group; which comprises the steps of:

(1) culturing Streptomyces sp. A93017, or a glucuronidating mutant thereof, in a nutrient medium containing assimilable sources of carbon, nitrogen, and inorganic salts, and a substrate compound of the formula

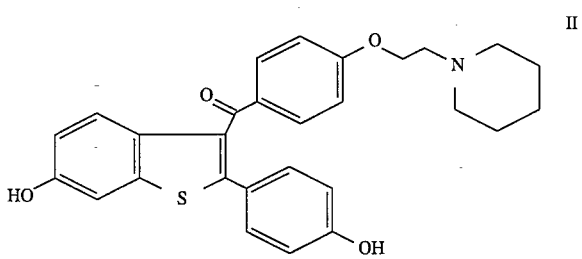

under submerged aerobic conditions until a substantial level of said compounds are produced; and (2) separating said compounds from the nutrient medium.

DETAILED DESCRIPTION OF THE INVENTION

The present invention relates to a novel process for the preparation of certain benzo[b]thiophene glucuronides. This novel process comprises fermentation of the microorganism Streptomyces sp. A93017, or a glucuronidating mutant thereof, in the presence of a substrate compound of the formula

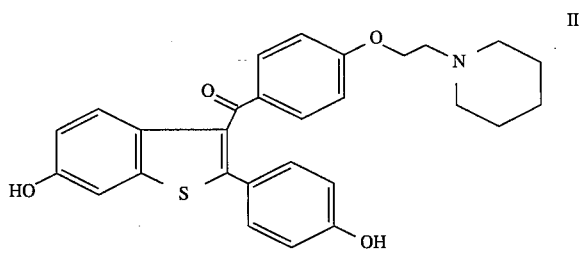

producing the β-glucuronidated biotransformation products. The biotransformation products of this process are the 6 -β-glucuronide, the 4'-β-glucuronide, and the 6,4-di-β-glucuronide, which are shown below:

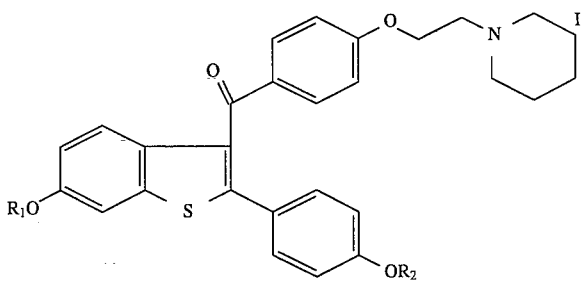

wherein β-glu is a β-glucuronide group of the formula

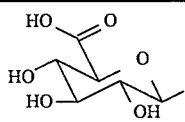

| compound | R₁ | R₂ |
|---|---|---|
| 6-glucuronide | β-glu | H |
| 4' glucuronide | H | β-glu |
| 6,4'-diglucuronide | β-glu | β-glu |

The novel process of the present invention comprises fermentation of the microorganism Streptomyces sp. A93017, or a glucuronidating mutant thereof, in a nutrient medium, and separation of the resulting biotransformation products, the compounds of formula I. The substrate compound, 6-hydroxy-2-(4-hydroxyphenyl)-3-[4-(2-piperidinoethoxy)benzoyl]benzo[b]thiophene, is prepared as described in U.S. Pat. No. 4,418,068, which is incorporated herein by reference.

A culture of A93017 is being deposited and made part of the stock culture collection of the Northern Regional Research Center, Agricultural Research, North Central Region, 1815 North University Street, Peoria ,Ill. 61604 from which it is available to the public under the accession number NRRL 21489 (*Streptomyces sp.*, deposited Aug. 1, 1995). A culture of this organism is currently available in the permanent culture collection of the American Type Culture Collection, 12301 Parklawn Drive in Rockville, Md., from which it is available under the accession number ATCC 55043. A general description of A93017, previously called HA6751, is fully described in U.S. Pat. No. 5,057,522, which is incorporated herein by reference.

As is the case with many microorganisms, the characteristics of *Streptomyces sp.* A93017 are subject to variation. Mutants of the strain may be obtained by methods known in the art, for example, by treatment with various physical and chemical mutagens such as ultraviolet light, X-rays, gamma rays, and chemicals such as N-methyl-N'-nitro-N-nitrosoguanidine. Natural and induced mutants of Streptomyces sp. A93017, which retain the ability to glucuronidate the substrate compound, are considered useful in the present invention. The processes for preparing the formula I compounds by fermentation of glucuronidating mutants of A93017 are considered an aspect of this invention.

In general, the formula I compounds can be produced by culturing (fermenting) the above-described microorganism in the presence of an appropriate concentration of substrate compound (II) in an aqueous nutrient medium containing assimiable sources of carbon, nitrogen, and inorganic salts, preferably under submerged aerobic conditions (e.g., shaking culture and submerged culture). The substrate compound may be added as the free base form, or as an acid addition salt. These acid addition salts are prepared as described in U.S. Pat. No. 4,418,068, which is incorporated herein by reference. The preferred acid addition salt is the hydrochloride salt. An appropriate concentration of the substrate compound in the aqueous medium ranges from 0.05 mg/ml to 1.0 mg/ml, preferably 0.5 mg/ml. The medium is incubated at a temperature between 25° C. and 35° C., preferably 30° C.; culture growth will be inhibited and culture death will occur outside of this range. The aqueous medium is incubated for a period of time necessary to complete the biotransformation as monitored by high performance liquid chromatography (HPLC) or liquid chromatography/mass spectroscopy (LC/HS) usually for about 24 hours to about 48 hours, on a rotary shaker operating at about 250 rpm with a throw of two inches. When the biotransformation is performed in fermentation tanks, the process is usually complete after about 48 hours to about 60 hours. Preferably, additional raloxifene (0.5 mg/mL) is added to the fermentation tanks at about 12 hours to about 16 hours. If additional raloxifene is added, the fermentation tanks are harvested at about 72 hours to about 96 hours.

The aqueous medium is maintained at a pH between 6 and 8, preferably about 7, at the initiation and termination (harvest) of the fermentation process. The desired pH may be maintained by the use of a buffer such as morpholinoethanesulfonic acid (MES), morpholinopropanesulfonic acid (MOPS), and the like, or by choice of nutrient materials which inherently possess buffering properties, such as vegetative and production media described herein below. Alternatively, the pH can be adjusted prior to, during, or after fermenting the organism by the addition of ammonium hydroxide or sodium hydroxide.

The culture medium used to grow the Streptomyces sp. A93017 can be any one of a number of media. For economy in production, optimal yield, and ease of product isolation, however, certain culture media are preferred.

The preferred sources of carbon in the nutrient medium are certain carbohydrates such as glucose, xylose, galactose, glycerin, starch, dextrin, and the like. Other sources which may be included are maltose, rhamnose, raffinose, arabinose, mannose, mannitol, salicin, sodium succinate, molasses, and the like. Preferably, the carbon sources are glucose, molasses, and starch. The most preferred carbon source is glucose. When the biotransformation is performed in fermentation tanks, additional glucose is added preferably as a continuous feed, beginning at about 16 hours to about 22 hours postinoculation, at a rate of about 25 g/L/day.

The preferred sources of nitrogen are yeast extract, meat extract, meat peptones, gluten meal, cottonseed meal, soybean flour or meal and other vegetable meals (partially or totally defatted), enzyme-hydrolyzed casein ( e.g. N-Z-Amine A, Sheffield Chemical Co., Norwich, N.Y. ), soybean hydrolysates, yeast hydrolysates, corn steep liquor, dried yeast, wheat germ, feather meal, peanut powder, distiller's solubles, as well as inorganic and organic nitrogen compounds such as ammonium salts (e.g. ammonium nitrate, ammonium sulfate, and ammonium phosphate), urea, amino acids, and the like. The preferred nitrogen sources are yeast extract, soybean flour, and enzyme-hydrolyzed casein.

Nutrient inorganic salts are added also to the culture medium. Among the nutrient inorganic salts are the customary soluble salts capable of yielding zinc, sodium, iron, potassium, magnesium, calcium, ammonium, chloride, carbonate, sulfate, nitrate, and the like ions. Preferably, calcium carbonate, potassium chloride, magnesium sulfate, and iron sulfate are added to the culture medium.

Essential trace elements necessary for the growth and development of the organism should also be included in the culture medium. Such trace elements commonly occur as impurities in other substituents in the medium in amounts sufficient to meet the growth requirements of the organism.

The carbon and nitrogen sources need not be used in their pure form because less pure materials which contain traces of growth factors and considerable quantities of mineral nutrients are also suitable for use. If necessary, especially when the culture medium foams, a small amount (e.g. 0.5 mL/L) of an anti-foam agent, such as liquid paraffin, fatty oil, plant oil, mineral oil, polypropylene glycol, or silicone may be added.

Submerged aerobic cultural conditions are preferred for the production of the formula I compounds in substantial amounts. For the production in small amounts, a shake-flask or surface culture is employed. Furthermore, when the growth is carried out in large tanks, it is preferable to use the vegetative form of the organism for inoculation in the production tanks in order to avoid growth lag in the process of production of the formula I compounds. Accordingly, it is desirable first to produce a vegetative inoculum of the organism by inoculating a relatively small quantity of culture medium with spores or mycelia of the organism product in a "slant" or shake flask, and culturing said inoculated medium, also called the "vegetative medium". The cultured vegetative inoculum is then transferred aseptically to large tanks. The fermentation medium, in which the inoculum is produced, is substantially the same as or different from the medium utilized for the production of the formula I compounds and is generally autoclaved to sterilize the medium prior to inoculation. The fermentation medium is generally adjusted to a pH between 6 and 8, preferably about 7, prior to the autoclaving step by suitable addition of an acid or base, preferably in the form of a buffering solution.

The temperature of the vegetative medium is maintained between 25° C. and 35° C., preferably 30° C.; culture growth will be inhibited and culture death will occur outside of this range. Incubation of the vegetative medium is usually conducted for a period of about 24 hours to about 72 hours, preferably 48 hours, on a rotary shaker operating at 250 rpm; the length of incubation time may be varied according to fermentation conditions and scales.

As is customary in submerged aerobic culture processes, sterile air is blown into the vessel from the bottom while the medium is stirred with conventional turbine impellers. The maximum oxygen uptake of the fermentation under the conditions used thus far has not exceeded about 0.4 mmol/L/minute. In a fully baffled 150-liter fermentor containing approximately 110 liters of broth, an initial aeration rate of 0.5 scfm with an agitation rate of 150 rpm is sufficient to maintain the level of dissolved oxygen at or above 30% of air saturation at a pressure of 0.34 atmospheres. If the dissolved oxygen level falls below 30%, the air flow and agitation should be increased.

Biotransformation of the formula I compound can be followed during the fermentation by assaying samples of the broth using high performance liquid chromatography (HPLC) or liquid chromatography/mass spectroscopy (LC/MS). The HPLC system included a Waters RCM (8mm ×10mm) with a Waters NOVAPak C18 cartridge and a Waters μ BondaPak C18 guard column (Millipore Corp., Milford, Mass.), eluting with a gradient solvent system as shown below:

| Gradient Solvent System (HPLC) | | |
|---|---|---|
| Time (min.) | A (%) | B (%) |
| 0 | 85 | 15 |
| 5 | 85 | 15 |
| 25 | 50 | 50 |
| 30 | 50 | 50 |
| 33 | 85 | 15 |

A: 0.2% trifluoroacetic acid in MilliQ water
B: 0.2% trifluoroacetic acid in acetonitrile.

The solvent flow rate was 1 mL/min. The retention times for the compounds were measured with a UV detector at 290 nm, and were compared with authentic samples of the various glucuronides.

The LC/MS system included a Waters 600-MS solvent delivery and control system with a M991 photo diode assay detector (UV). The column was a Waters RCM (8mm ×10mm) with a Waters NOVAPak C18 cartridge and a Waters μBondaPak C18 guard column. The flow from the column (1 mL min) was split such that about 50 μL/min flowed into the mass spectrometer. The mass spectrometer was a VG/Fisons Quattro triple quadrupole mass spectrometer with ion formation by pneumatically assisted electrospray interface. The gradient solvent system is shown below:

| Gradient Solvent System (LC/MS) | | |
|---|---|---|
| Time (min.) | A (%) | B (%) |
| 0 | 100 | 0 |
| 5 | 100 | 0 |
| 20 | 0 | 100 |
| 30 | 0 | 100 |
| 33 | 100 | 0 |

A: Acetonitrile/Water/Trifluoroacetic acid (15/85/0.2, v/v)
B: Acetonitrile/Water/Trifluoroacetic acid (50/50/0.2, v/v).

The biotransformation products, formula I compounds, are recovered from the culture medium by conventional means which are commonly used in the fermentation art for the recovery of other biologically-active substances. The formula I compounds are found in the cultured mycelial mass and in the filtered broth, which are obtained by filtering or centrifuging the cultured broth. Accordingly, the formula I compounds can be separated and purified from the mycelium and the filtrate by conventional methods, such as concentratton under reduced pressure, lyophilization, extraction with a conventional solvent (such as methanol, ethyl acetate, methylene chloride, and the like), pH adjustment, treatment with a conventional resin (e.g. anion or cation exchange resin, nonionic adsorption resin), treatment with a conventional adsorbent (e.g. activated charcoal, silicic acid, silica gel, cellulose, alumina), crystallization, recrystallization, and the like.

Maximum recovery of the biotransformation products is accomplished by diluting the whole broth with an organic solvent, such as methanol, and filtering the resulting mixture to separate the broth from the mycelial mass. The mycelial mass is discarded, and the filtered broth is processed to give the formula I compounds.

A variety of techniques may be used in purification of lid the formula I compounds. A preferred technique for purification of the filtered broth is the use of adsorption chromatography. A nonionic adsorption resin, such as HP-20 or HP-20ss (Mitsubishi Kasei America Inc., White Plains, N.Y.), are preferred for this purification. Generally, the filtered broth is diluted with water, and applied to column containing HP-20 or HP-20ss. The column is eluted with a linear gradient of methanol/0.5% aqueous ammonium acetate (25:75, pH 9.0) to methanol/0.5% aqueous ammonium acetate (70:30, pH 9.0). The eluent containing the formula I compounds are easily identified using HPLC.

When the broth and mycelial mass are separated without extraction of the biotransformation products by addition of an organic solvent, the mycelial is processed to obtain additional quantities of the biotransformation products. A preferred method of processing the mycelial mass is to extract the separated mycelial filter cake with a suitable solvent, such as acetone, acetonitrile, ethyl acetate, or methanol. The extracting solvent is then evaporated to give a concentrated aqueous solution. The formula I compounds are separated from this solution using a procedure that is similar to that described above.

The biotransformation products are further purified by similar procedures. For example, the compounds may be chromatographed on nonionic adsorption resin (e.g. HP-20ss or HP-20) or on silica gel.

In order to illustrate more fully the operation of the present invention, the following examples are provided:

EXAMPLE 1

Shake-Flask Fermentation of A93017

The culture Streptomyces sp. A93017, as frozen vegetative mycelia, was thawed and used to inoculate a vegetative medium (50 mL) having the following composition:

| Vegetative Medium | g/L |
|---|---|
| glucose | 5.0 |
| soluble starch | 10.0 |
| yeast extract | 2.5 |
| enzyme-hydrolyzed casein* | 2.5 |
| calcium carbonate | 0.5 |
| potassium chloride | 0.2 mg |
| magnesium sulfate heptahydrate | 0.2 mg |
| iron (II) sulfate heptahydrate | 0.004 mg |
| distilled water | 1.0 L |
| adjust pH to 7.0–7.5 with sodium hydroxide | |

*N—Z-Amine A (Sheffield Chemical Co., Norwich, New York)

The inoculated vegetative medium was incubated in a 250-mL Erlenmeyer flask at 30° C. for about 17 hours on a shaker orbiting in a two-inch circle at 250 rpm. This incubated vegetative medium (0.5–2 mL) was used to inoculate a production medium (50 mL) containing raloxifene at a final concentration of 0.5 mg/mL. The production medium had the following composition:

| Production Medium | g/L |
|---|---|
| soybean flour | 15.0 |
| enzyme-hydrolyzed casein* | 1.0 |
| glucose | 25.0 |
| cane molasses | 3.0 |
| calcium carbonate | 2.5 |
| potassium chloride | 0.2 mg |
| magnesium sulfate heptahydrate | 0.2 mg |
| iron (II) sulfate heptahydrate | 0.004 mg |
| distilled water | 1.0 L |
| adjust pH to 7.2–7.5 with sodium hydroxide | |

*N—Z-Amine A

The inoculated production medium was incubated in a 250-mL wide-mouth Erlenmeyer flask at 30° C. for about 28 hours to about 48 hours on a shaker orbiting in a two-inch circle at 250 rpm. Methanol extracts of the whole broths were examined by LC/MS for the presence of the biotransformation products. The molecular weights obtained on the biotransformation products were consistent with the molecular weights established for authentic samples of the monoglucuronides of raloxifene.

EXAMPLE 2

Tank Fermentation of A93017

In order to provide a larger volume of inoculum, a suspension of A93017 maintained in liquid nitrogen was thawed, and a 1-mL sample was used to inoculate a first-stage vegetative medium (50 mL) in a 250-mL Erlenmeyer flask. The pH was adjusted to pH 7.0 prior to sterilization. The first-stage vegetative medium had the following composition:

| First-Stage Vegetative Medium | g/L |
|---|---|
| glucose | 15.0 |
| yeast extract | 7.5 |
| enzyme-hydrolyzed casein* | 7.5 |
| soluble starch | 30.0 |
| calcium carbonate | 1.5 |
| pH was adjusted to pH 7.0 with sodium hydroxide | |

*N—Z-Amine A

The inoculated medium was incubated at 30° C. for about 48 hours on a shaker orbiting in a two-inch circle at 250 rpm. A 10-mL sample of the inoculated first-stage vegetative medium was used to inoculate a second-stage vegetative medium (400 mL) having the same composition as the first. This second-stage medium was incubated in a 2-L Erlenmeyer flask at 30° C. for about 48 hours on a shaker orbiting in a two-inch circle at 250 rpm. Five second-stage cultures (about 2L) were used to inoculate 110 L of sterile production medium/see Example 1). Antifoam 471 (SAG 471, Union Carbide, Danbury, Conn.) was added to the production medium at 0.25/L. Ammonium hydroxide was used to maintain the pH at 7.0. The inoculated production medium was allowed to ferment in a 150-L stirred fermentation tank at a temperature of 30° C. and at pH 7.0. The substrate compound, raloxifene, was added at the beginning of the tank fermentation at a concentration of 0.5 g/L. The tank was initially stirred at a rate of 150 rpm, then ramped from 150 rpm to 425 rpm beginning at the 12th hour and ending at the 17th hour postinoculation. The dissolved oxygen level was controlled by the addition of sterile air at an initial rate of 0.5 scfm, then increasing the rate to 3.5 scfm beginning at the 12th hour and ending at the 17th hour post-inoculation. Two fermentation tanks were prepared. In the first tank, additional raloxifene (50 g) was added at 16 hours and a glucose (25 g/L/day) feed began at 22 hours. In the second tank, additional raloxifene (50 g) was added at 22 hours, and a glucose (25 g/L/day) feed began at 23 hours. Both tanks were harvested at about 66 hours postinoculation.

Example 3

Purification of the Glucuronides

The whole fermentation broth, prepared as described in Example 2, was treated with methanol (115 L), and stirred for about 15 minutes. The resulting slurry was filtered through a 30 ft$^2$ ceramic filter unit. The enriched broth/methanol extract contained the glucuronides and substrate compound. This broth extract was diluted with water (400 L) and added to a column containing 10 L of HP-20ss at a flow rate of 1 L/min. The column was eluted with a linear gradient of methanol/0.5% aqueous ammonia acetate (25:75, pH 9) to methanol/0.5% aqueous ammonium acetate (50:50, pH 9) over two minutes, at a flow rate of 1 L/min. Then the gradient was increased to methanol/0.5% aqueous ammonium acetate (70:30, pH 9) over 90 minutes, at a flow rate of 1 L/min. The eluate was collected in 4-L fractions. These 4-L fractions were assayed by HPLC to identify the fractions containing the formula I compounds: pool 1, fraction 3, contained the 6,4'-diglucuronide; pool 2, fractions 11–15, contained the 6-glucuronide as the major component of the mixture; pool 3, fractions 16–17, contained a mixture of the 4'-glucuronide and the 6-glucuronide in a ratio of about 3:2, respectively; and pool 4, fractions 18–25, contained the 4'-glucuronide as the major component.

Pool 4 was concentrated from about 25 L to about 5.5 L, and the pH adjusted to 8.5 by the addition of concentrated ammonium hydroxide. This solution was added to a column containing HP-20ss (10 L). The column was eluted with a linear gradient of methanol/0.5% aqueous ammonium acetate (45:55, pH 9.0) to methanol/0.5% aqueous ammonium acetate (70:30, pH 9.0) over 100 minutes, at a flow rate of 1 L/min. One-liter fractions were collected and examined by HPLC. The fractions containing the formula I compounds were combined on the basis of the HPLC analysis into two pools. Pool 4A contained 0.85 g of the 4'-glucuronide at 67% purity and pool 4B contained 6.3 g of the 4'-glucuronide at 91.5% purity. The pools were treated with additional HP-20ss resin (500 g), and the resulting mixture stirred. The substrate compound, raloxifene, preferentially adsorbed to the resin, while the 4'-glucuronide remained in solution. The resin was removed by filtration and the filtrate, containing the 4'-glucuronide, was treated with additional HP-20ss (250 g). The resulting mixture was stirred and treated with an equal volume of water to adsorb the 4'-glucuronide onto the resin. An additional portion of HP-20ss resin (150 g) was added The resulting mixture was added to a column and eluted with methanol (3×1 L). The first and second methanol eluates were combined and concentrated to about 250 mL. The residue was treated with water (250 mL), causing the 4'-glucuronide to come out of solution. This mixture was treated with methanol (550 mL) to redissolve the 4'-glucuronide, and the resulting solution allowed to stand. The 4'-glucuronide precipitated from this solution. The precipitate was collected by filtration, dried in vacuo at 40° C., to give 2.45 g of the 4'-glucuronide.

Pool 3 was concentrated from about 7 L to about 3.5 L, and treated with methanol to dissolve the precipitated material. The resulting solution was adjusted to pH 8.5 by the addition of concentrated ammonium hydroxide, and added to an HP-20ss resin column. The column was eluted with a gradient of methanol/0.5% aqueous ammonium acetate (50:50, pH 8.5) to methanol/0.5% aqueous ammonium acetate (65:45, pH 8.5) over 100 min, at a flow rate of 1 L/min. The eluate was collected in 4-L fractions and each fraction was analyzed by HPLC. The following pools were made on the basis of HPLC: pool 3A (fractions 9–13), pool 3B (fractions 14–16), and pool 3C (fractions 17–21). Pool 3C was added to HP-20ss resin (250 g), and treated with an equal volume of water (16 L). The resulting mixture was filtered and the filtrate discarded. The resin was placed in a column and eluted with methanol (4×500 mL). The first and second eluates were combined and concentrated to about 250 mL. The resulting cloudy solution was treated with water (150 mL) and methanol (50 mL), then stirred for one hour. The resulting precipitate was collected by filtration, and dried in vacuo at 50° C. to give 1.78 g of the 4'-glucuronide. Pool 3A was treated in a manner similar to that for Pool 3C, to give 2.66 g of the 6-glucuronide.

Pool 2 was concentrated from about 17 L to about 6 L. The pH of the resulting mixture was adjusted to pH 8.5 with concentrated ammonium hydroxide. The concentration step produced gummy solids that would not dissolve upon treatment of the mixture with methanol. The solids were removed by filtration and dried to give 8.1 g of a 85:15 mixture of the 4'-glucuronide and the 6-glucuronide, respectively. The concentrated solution was added to a column containing HP-20ss at a flow rate of 1 L/min. This column was eluted with a linear gradient of methanol/0.5% aqueous ammonium acetate (50:50, pH 8.5) to methanol/0.5% aqueous ammonium acetate (60:40, pH 8.5) over 90 min, at a flow rate of 1 L/min. The eluate was collected in 4-L fractions, and analyzed using HPLC. Based on the HPLC analysis, the following pools were made: pool 2A (fractions 14–18), pool 2B (fractions 19–23), and pool 2C (fractions 24–27). Pool 2A was treated with methanol-washed HP-20ss resin (250 g) and water (14 L). The resulting mixture was filtered and the filtrate discarded. The resin was added to a column and eluted with methanol (2×1 L). The combined methanol eluates were concentrated to about 700 mL then treated with an equal volume of water with stirring. After about one hour, the resulting precipitate was filtered, and dried in vacuo to give 5.1 g of the 6-glucuronide. The mother liquor was treated with additional water (50 mL). The resulting precipitate was collected by filtration, and dried in vacuo to give 0.75 g of 6-glucuronide.

The dry precipitate isolated from pool 2A was combined with the precipitate isolated from pool 3A and treated with acetonitrile (250 mL). After stirring for ten minutes, the resulting mixture was filtered, and the precipitate was dried at 50° C. to give 8.3 g of 6-glucuronide (99% pure by HPLC).

6-glucuronide $^1$H NMR ($d_6$-DMSO): δ9.83 (1H, 7.73 (1H), 7.65 (2H), 7.33 (1H), 7.20 (2H), 7.06 (1H), 6.91 (2H), 6.69 (2H), 5.10 (1H) 4.11 (2H), 3.83 (1H), 3.34 1H), 3.32 (1H), 3.29 (1H), 2.74 (2H), 2.52 (2H), 1.50 (2H), 1.38 (2H). $^{13}$C NMR ($d_6$-DMSO): δ192.29, 170.56, 162.67, 158.04, 154.83, 142.39, 138.72, 134.32, 131.78, 129.78, 129.65, 129.50, 123.46, 123.11, 116.11, 115.70, 114.53, 108.48, 100.21, 76.01, 74.96, 72.94, 71.50, 65.37, 56.65, 54.00, 24.99, 23.40.

The dry precipitates isolated from pools 33 and 3C were combined, and the combination treated with acetonitrile (250 mL). After about ten minutes, the resulting mixture was filtered, and the solids were dried at 50° C. to give 4.0 g of the 4'-glucuronide (99% pure by HPLC).

4'-glucuronide $^1$H NMR ($d_6$-DMSO): δ9.84 (1H), 7.63 (2H), 7.42 (1H), 7.37 (1H), 7.22 (1H), 6.89 (2H), 6.85 (2H), 5.00 (1H), 4.18 (1H), 4.12 (1H), 3.66 (1H), 3.26 (2H), 3.19 (1H), 2.92 (2H), 2.73 (2H), 1.60 (2H), 1.43 (2H).

$^{13}$C NMR (d6-DMSO): δ191.92, 171.50, 162.24, 156.98, 155.57, 140.90, 139.48, 132.08, 131.79, 130.04, 129.79, 129.50, 126.56, 123.66, 116.03, 115.33, 114.39, 107.04, 98.88, 76.02, 75.10, 72.82, 71.65, 64.72, 55.70, 53.51, 24.02, 22.74.

Pool 1 was concentrated and added to a column (5 cm×50 cm) of HP-20ss resin at a flow rate of 50 mL/min. This column was washed with water, and eluted with a gradient of 0.05% ammonium acetate to 50% acetonitrile over 60 min. The fractions were analyzed by HPLC. Based upon the HPLC analysis, the fractions containing the 6,4'-diglucuronide were combined, concentrated, and lyophilized. The resulting lyophilized solid was dissolved in water (20 mL) and added to a column (7×40 cm) of HW40C resin (Toso Haas, Montgomeryville, Pa.). This column was eluted with water, and the fractions analyzed by HPLC. Based upon the HPLC analysis, the fractions containing the 6,4'-diglucuronide were combined, concentrated, and lyophilized. The residue was purified using reverse-phase HPLC (C-18 column) using a gradient of acetonitrile/0.05% aqueous ammonium acetate (90:10) to acetonitrile/0.05% aqueous ammonium acetate (70:30) over 20 to 30 min. The eluate containing the 6,4'-diglucuronide was desalted using reverse-phase HPLC (C-18 column) and a methanol/water gradient to give about 200 mg of the diglucuronide.

6,4'-diglucuronide $^1$H NMR ($D_2O$): δ7.64 (1H), 7.47 (2H), 7.32 (1H), 7.05 (3H), 6.79 (2H), 6.65 (2H), 5.09 (1H), 4.84 (1H), 4.14 (2H), 3.95 (1H), 3.86 (1H), 3.75 (3H), 3.69 (1H), 3.65 (1H), 3.62 (1H), 3.41 (2H), 3.38 (2H), 2.87 (2H), 1.83 (2H), 1.76 (1H), 1.68 (2H), 1.41 (1H).

$^{13}$C NMR (D20): δ194.4, 174.5, 161.9, 157.3,155.0, 146.1, 139.8, 135.1, 132.7, 130.7, 130.6, 130.0, 127.6, 124.1, 116.9, 116.6, 114.7, 109.7, 101.3,100.2, 76.3, 76.2, 75.8, 75.7, 73.2, 73.0, 72.0, 71.9, 62.1, 55.1, 53.7, 22.7, 21.2.

The following test procedures illustrate the pharmaceutical activity of the formula I compounds, the biotransformation products of the present invention.

Test Procedure 1

A postmenopausal model was used in which effects of different treatments upon circulating lipids, uterine weight, and EPO activity were determined.

Seventy-five day old female Sprague Dawley rats (weight range of 200 to 225 g) were obtained from Charles River Laboratories (Portage, Mich.). The animals were either bilaterally ovariectomized (OVX) or exposed to a sham surgical procedure at Charles River Laboratories, and then shipped after one week. Upon arrival, they were housed in metal hanging cages in groups of three or four per cage and had ad libitum access to food (calcium content approximately 0.5%) and water for one week. Room temperature was maintained at 22.2° ±1.7° C. with a minimum relative humidity of 40%. The photoperiod in the room was 12 hours light and 12 hours dark.

Dosing Regimen/Tissue Collection. After a one-week acclimation period (two weeks post-OVX), daily dosing with test compound was initiated. All compounds were administered subcutaneously at the dosages listed. Animals were dosed daily for four days. Following the dosing regimen animals were weighed and anesthetized with a ketamin-exylazine (2:1, V/V) mixture, and a blood sample was collected by cardiac puncture. The animals were then sacrificed by asphyxiation with $CO_2$, the uterus was removed through a midline incision, and a wet weight of the excised uterus was determined.

Cholesterol Analysis. Blood samples were allowed to clot at room temperature for two hours, and serum was obtained following centrifugation for ten minutes at 3000 rpm. Serum cholesterol was determined using a high performance cholesterol assay obtained from Boehringer Mannheim Diagnostics (Indianapolis, Ind.). Briefly the cholesterol was oxidized to cholest-4-en-3-one and hydrogen peroxide. The hydrogen peroxide was then reacted with phenol and 4-aminophenazone in the presence of peroxidase to produce a p-quinoneimine dye, which was read spectrophotometrically at 500 nm. Cholesterol concentration was then calculated against a standard curve.

Uterine Eosinophil Peroxidase (EPO) Assay. The presence of eosinophils in the uterus is an indication of estrogenic activity of a compound. To maintain EPO activity, uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM o-phenylenediamine (final concentrations) in Tris buffer, increase in absorbance was monitored for one minute at 450 nm. The maximal velocity of a 15 sec interval was determined over the initial linear portion of the reaction curve.

The results of treatments are presented below. In summary, ovariectomy of the rats caused an increase in serum cholesterol as compared to intact vehicle treated controls in these studies, the compounds caused a serum cholesterol decrease in a dose dependent manner; however, only minimal increase of uterine weight and little or no stimulation of EPO activity over the ovariectomized controls was present in treated animals.

| Compound | Dose (mg/kg) | % Decrease of Serum Cholesterol[a] | % Uterine Wt. gain[b] | EPO Activity (n OD/min)[c] |
|---|---|---|---|---|
| 6-glu | 0.013 | 21.7 | −21.3 | 2.0 |
|  | 0.13 | 43.8 | 14.2 | 2.3 |
|  | 1.3 | 44.5 | 24.1 | 3.5 |
| 4'-glu | 0.013 | 13.6 | −7.7 | 3.2 |
|  | 0.13 | 21.9 | 14.5 | 3.1 |
|  | 1.3 | 56.8 | 36.1 | 4.4 |

[a]Percent decrease of serum cholesterol equals (serum cholesterol of treated OVX animals minus serum cholesterol of OVX animals) divided by (serum cholesterol of control OVX animals) multiplied by 100.
[b]Percent uterine weight gain equals (uterine weight of treated OVX animals minus uterine weight of control OVX animals) divided by (uterine weight of control OVX animals) multiplied by 100.
[c]$V_{max}$ for eosinophil peroxidase activity.

Test Procedure 2

To mimic the in vivo environment for inhibition of bone loss, a rat marrow culture technique which acts as an osteoclast differentiation model (in the absence of 1,25-vitamin D and in the presence of bone) was used. It has been found that marrow cells from neonatal rat long bones will differentiate and resorb significant amounts of bone over a 4-day period in the presence of 0.1 μg/ml IL-6. Specifically, marrow cells from 2-day old neonares were cultured on bone slices at a density of $2 \times 10^5/cm^2$ in 199 media (Gibco, Gaithersburg, Md.) with 20% heat inactivated fetal bovine serum (Gibco) and 0.1 μg/ml IL-6 for four days. After incubation, bone slices were devitalized, fixed, dehydrated, and stained with 1% toluidine blue in 1% sodium borate for one minute. Resorption lacunae were quantitated by reflected polarized light microscopy. The compounds inhibited this cytokine stimulated resorption with $IC_{50}$s of about 10mM.

We claim:
1. A process for preparing a compound of the formula

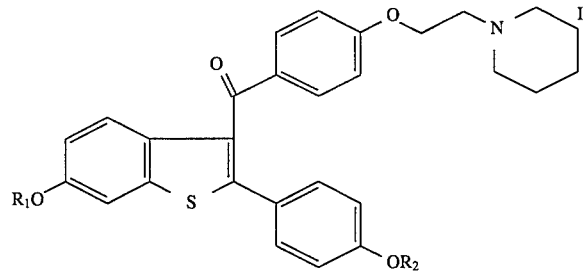

wherein $R_1$ and $R_2$ are hydrogen or a β-glucuronide group of the formula

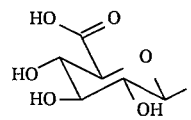

provided at least one of $R_1$ and $R_2$ is a β-glucuronide group; which comprises the steps of:
(1) culturing Streptomyces sp. A93017, or a glucuronidating mutant thereof, in a nutrient medium containing assimilable sources of carbon, nitrogen, and inorganic salts, and a substrate compound of the formula

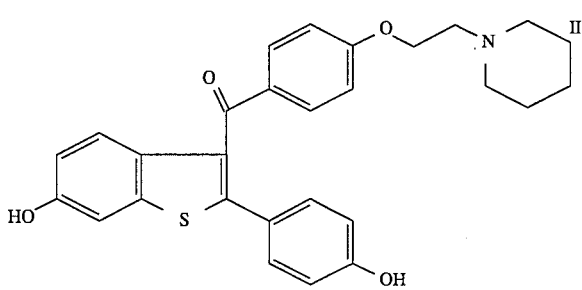

under submerged aerobic conditions until a substantial level of said compounds are produced; and (2) separating said formula I compound from the nutrient medium.

2. The process of claim 1 wherein Streptomyces sp. A93017 is used.

3. The process of claim 2 wherein A93017 is cultured at about 30° C. for about 24 hours to about 96 hours.

4. The process of claim 2 wherein additional substrate compound is added to the nutrient medium in step (1).

5. The process of claim 2 wherein the source of carbon is glucose.

6. The process of claim 5 wherein additional glucose is added as a continuous feed in step (1).

7. The process of claim 2 wherein the compound of the formula

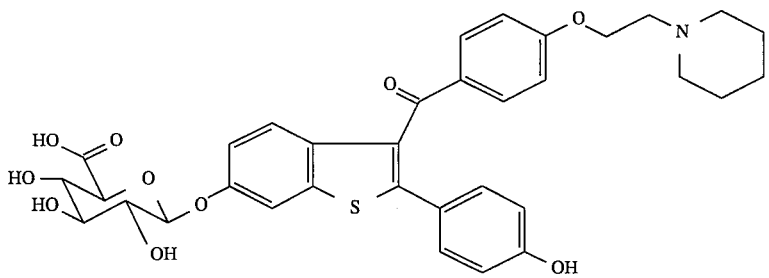

is produced.

8. The process of claim 2 wherein the compound of the formula

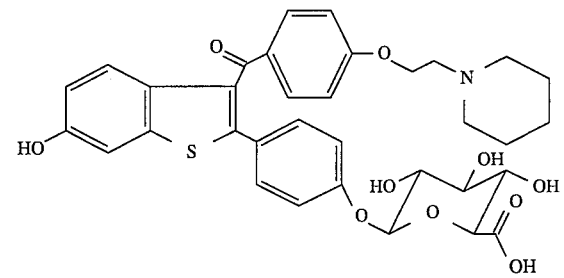

is produced.

9. The process of claim 2 wherein the compound of the formula

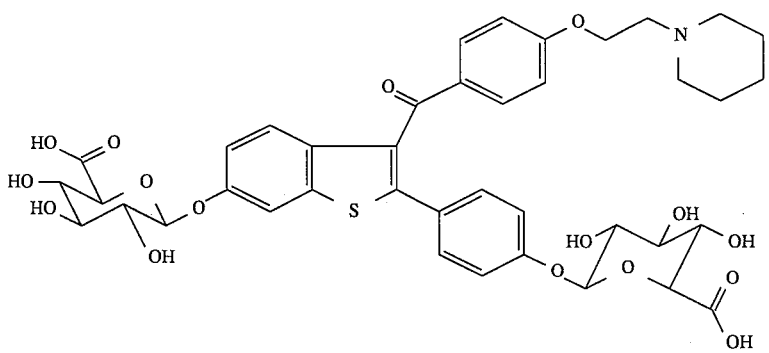

is produced.

* * * * *